US006846784B2

(12) United States Patent
Engel et al.

(10) Patent No.: US 6,846,784 B2
(45) Date of Patent: Jan. 25, 2005

(54) WATER SOLUBLE POUCH PACKAGE

(75) Inventors: Steven P. Engel, Rockford, MI (US); Jesse C. Leverett, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 188 days.

(21) Appl. No.: 10/354,654

(22) Filed: Jan. 30, 2003

(65) Prior Publication Data

US 2004/0152610 A1 Aug. 5, 2004

(51) Int. Cl.[7] ............................................... C11D 17/04
(52) U.S. Cl. .................. 510/120; 510/130; 510/439; 510/475; 510/477; 510/509; 424/400; 424/409
(58) Field of Search .................. 510/120, 130, 510/439, 475, 477, 509; 424/400, 409

(56) References Cited

U.S. PATENT DOCUMENTS

| 3,322,674 | A |   | 5/1967  | Friedman       |         |
|-----------|---|---|---------|----------------|---------|
| 4,522,738 | A |   | 6/1985  | Magid et al.   |         |
| 4,659,495 | A | * | 4/1987  | Figliola       | 424/401 |
| 5,116,388 | A |   | 5/1992  | Brooks         |         |
| 5,132,036 | A | * | 7/1992  | Falou et al.   | 510/277 |
| 5,780,418 | A | * | 7/1998  | Niinaka et al. | 510/439 |
| 5,783,541 | A | * | 7/1998  | Tack et al.    | 510/224 |
| 5,830,543 | A | * | 11/1998 | Miyake et al.  | 428/35.2 |
| 5,839,842 | A | * | 11/1998 | Wanat et al.   | 401/201 |
| 5,863,885 | A | * | 1/1999  | Ruggieri et al.| 510/439 |
| 6,106,849 | A |   | 8/2000  | Malkan et al.  |         |
| 6,326,339 | B1|   | 12/2001 | Rattinger et al.|        |
| 6,576,604 | B1| * | 6/2003  | Hoshino et al. | 510/438 |
| 6,683,041 | B1| * | 1/2004  | Nissing et al. | 510/438 |
| 6,727,215 | B2| * | 4/2004  | Roberts et al. | 510/296 |
| 2003/0114332 | A1 | * | 6/2003 | Ramcharan et al.| 510/296 |
| 2003/0192130 | A1 | * | 10/2003 | Kaaret et al.  | 8/115.51 |

FOREIGN PATENT DOCUMENTS

| EP | 0236136 A2 | * | 9/1987 |
| EP | 0700989    |   | 9/1994 |
| EP | 0941939    |   | 3/1999 |
| JP | 07267848 A | * | 10/1995 |
| JP | 07330580 A | * | 12/1995 |
| WO | WO9429104  |   | 12/1994 |

* cited by examiner

*Primary Examiner*—Lorna M. Douyon
(74) *Attorney, Agent, or Firm*—Warner Norcross & Judd

(57) ABSTRACT

A unit-dose personal care product including a cleansing agent and a cleansing pad wrapped in a film of water-soluble material. The water-soluble material protects the cleansing pad and cleansing agent until the package is exposed to water, at which time the film dissolves and the user is left with a cleansing product comprised of the pad, cleansing agent and water. Also disclosed is a method of manufacturing the personal care product.

13 Claims, 2 Drawing Sheets

WATER SOLUBLE POUCH PACKAGE

BACKGROUND OF THE INVENTION

The present invention relates to cleansing products and, more specifically, to cleansing products enclosed in water-soluble packages.

Unit-dose personal care products, particularly cleansing products, traditionally contain a ready to use product in a convenient dispensable package. In these products, a cleansing pad is wrapped inside a package. Usually, a wet cleansing agent is absorbed into the cleansing pad before packaging.

These pre-moistened products have a variety of problems. One of the most significant problems is that, over time, the cleansing product will dry up, rendering the product useless. This process is frequently hastened by the presence of even a slight leak in the packaging. This deters users from buying the products in bulk, or storing the products for a significant period of time.

Another problem is that the user must dispose of the package. After removing the product from the package, the package serves no further purpose. This results in a large amount of waste, especially if the consumer uses such products frequently. Further, the packaging can easily become litter if not disposed of properly.

Additionally some products may not be easily combined due to irregular compositions, such as powders and solids. In some other cases, products need to be kept separate until the time of use because of shelf life or compatibility issues. In these situations, it does not make sense to combine the cleansing pad with the cleanser because the user will not have a ready-to-use product.

SUMMARY OF THE INVENTION

The aforementioned problems are overcome by the present invention wherein a unit-dose cleansing product is provided with a cleansing pad and powder contained within a water soluble pouch.

In a preferred embodiment, the water-soluble pouch package includes a water-soluble film, a cleansing agent and a pad, such as a non-woven pad, loofah or sponge. The water-soluble film forms a pouch loosely containing both the cleansing agent and the pad. With this construction, when the pouch is exposed to water the water-soluble film dissolves. The cleansing pad absorbs the water and wetted cleansing agent to create a ready-to-use cleansing product.

In a more preferred embodiment, citric acid and sodium bicarbonate are added to the cleansing powder. The sodium bicarbonate and citric acid react to increase the foam of the cleansing product when the pouch is exposed to water. The increased foam aids in breaking down the water-soluble film and masking the presence of film residue.

The present invention provides a simple and inexpensive cleansing product. The water-soluble pouch package does not require complex packaging, and is much more economical and environmentally friendly than unit-dose products in packages that are not water soluble. The pouch in which the cleansing pad and cleansing agent are housed is broken down in the presence of water, thus eliminating any waste from the product packaging. Additionally, the present invention does not have shelf life or incompatibility problems.

Also disclosed is a method of making a unit-dose personal care product including the steps of (1) forming a film of water soluble material; (2) folding the film in half; (3) sealing the edges of the film to create a pouch; (4) inserting an amount of cleansing powder into the pouch; (5) inserting a cleansing pad into the pouch; and (6) sealing the pouch closed.

These and other objects, advantages, and features of the invention will be more readily understood and appreciated by reference to the detailed description of the preferred embodiment and the drawings.

DETAILED DESCRIPTION OF THE PREFERRED EMBODIMENT

Figure 1:
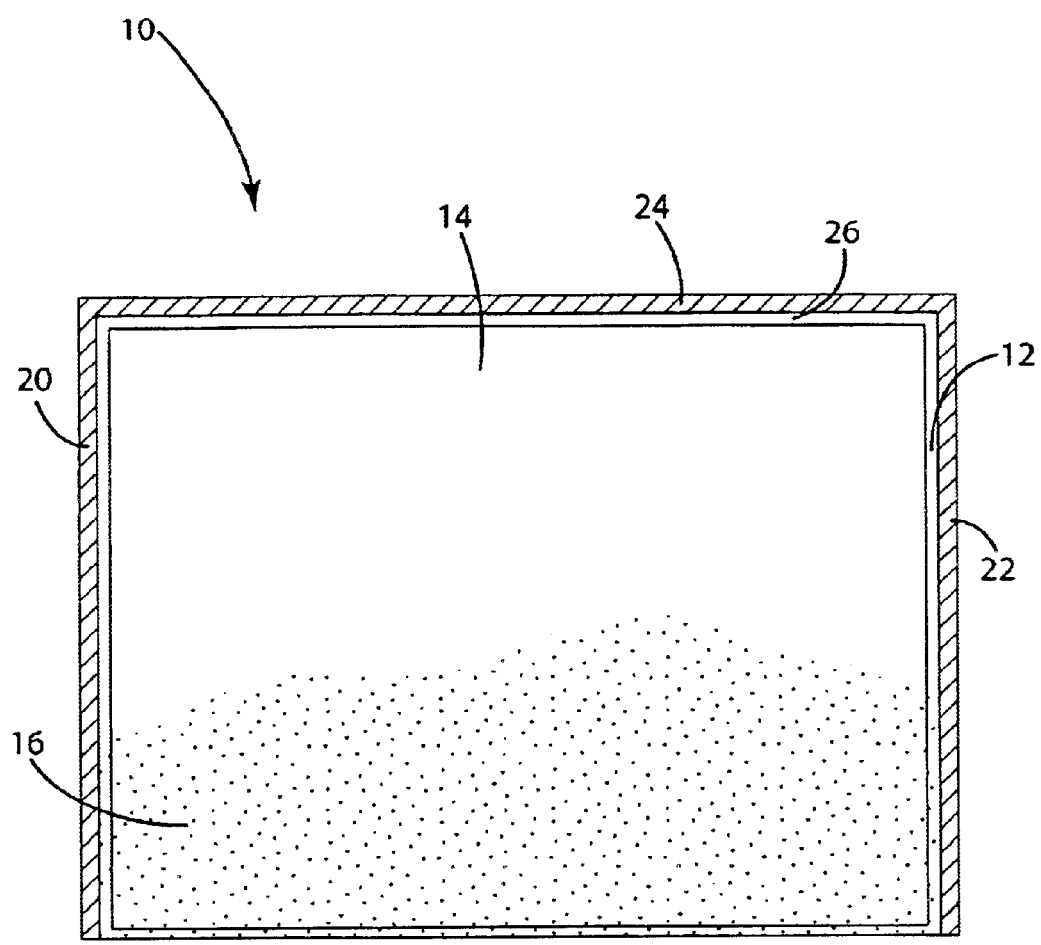
FIG. 1 is a top plan view of a water-soluble pouch package in accordance with the present invention.

A water soluble pouch package 10 in accordance with a preferred embodiment of the present invention is shown in FIG. 1. The package 10 generally includes a pouch 12, a pad 14 and a cleanser 16. The pouch 12 surrounds the pad 14 and cleanser 16. Though the invention will be described with respect to a water-soluble pouch containing a cleansing pad and cleansing agent, it will be understood by those skilled in the art that the invention is suitable for use in many applications, for example with hair dyes, sunscreens or insect repellant.

I. Apparatus

According to a preferred embodiment of the present invention, a pad 14 and predosed quantity of cleanser 16 are enclosed in pouch 12 to form a unit-dose cleansing package 10. The pouch 12 is made of a water-soluble film so that when the package is exposed to water, the film dissolves and the user is left with the combined pad 14 and cleanser 16. The pouch 12 can be composed of any water-soluble material that is sufficiently resilient to seal and protect the pad 14 and cleanser 16 during shipping and storage, but in a preferred embodiment the film 12 is made of a type of water-dissolvable polymer such as polyvinyl alcohol (PVOH). Alternative water-soluble materials include: water-soluble polyurethanes, such as polyvinylpyrrolidone (PVP); PVP copolymers, for example, vinyl pyrrilidone/vinyl acetate copolymers, such as PVP/vinyl acetate; water-soluble acrylic acid copolymers and their esters and salts, for example, the partial ester copolymers of acrylic/methacrylic acid and a polyethylene glycol ether of a fatty alcohol, such as acrylates/steareth-20 methacrylates copolymer available, for example, from Rohm & Haas under the trademark ACULYN 22; organic and inorganic salts of phenylbenzimidazole sulfonic acid (PSA), such as TEA-phenylbenzimidazole sulfonate and sodium phenylbenzimidazole sulfonate; water-soluble cellulosics, such as hydroxymethylcellulose, hydroxyethylcellulose, and hydroxypropylcellulose; water-soluble quaterniums, such as polyquaternium-7, polyquaternium-10, polyquaternium-37; carboxyvinyl polymers, such as carbomers and their salts, for example, sodium carbomer; and water-soluble polysaccharides, such as polydextrose and glucan.

The pad 14 is loosely contained in the pouch 12 and is capable of absorbing the cleanser 16 and water to create a foaming cleansing product. Any conventional cleansing pad can be used, such as a cloth, sponge or cut loofah. In the preferred embodiment the pad 14 is a non-woven cloth, and in a further preferred embodiment the non-woven cloth is composed of polyester and cellulose. The pad 14 is approximately the same shape as the pouch 12 to facilitate maximum absorption of the cleanser 16 by the pad 14. While the invention will be described in relation to a substantially square pad 14 and pouch 12, the invention is useful with pads and pouches of a variety of shapes.

The cleanser 16 is loosely enclosed in the pouch 12 along with the pad 14 and can be any desired cleansing agent, but is preferably a granulated cleansing agent. A granulated cleansing agent is preferred because it can most easily be combined with the pad 14 in the presence of water to produce a conventional cleansing product. However, other forms of cleansing products, such as cakes or gels, can also be used as desired. Further the cleansing product can be caked or otherwise pre-fixed to the pad. In the case of gels or liquids, the cleansing agent can be pre-absorbed by the pad. In a preferred embodiment the cleanser 16 is a surfactant powder consisting primarily of crystalline sorbitol and containing up to 2% polyethylene beads.

In a preferred embodiment, citric acid and sodium bicarbonate are added to the cleanser 16. These additives interact to produce foam, which both assists in breaking down the pouch 12 and increases the foam of the cleanser 16. Increased foam is a desirable characteristic of a cleansing product. Additionally, the foaming reaction causes the pouch 12 to break down more quickly and reduces the amount of film residue present on the cleansing product. The foam also masks the film residue. Other additives, such as aloe extract or fragrance, can be added as desired.

The construction of the package 10 is best illustrated in FIG. 1. The pouch 12 is a substantially rectangular pocket made of a film of water-soluble material. The dimensions of the pouch 12 are such that, when the left side 20, right side 22 and top 24 of the pouch 12 are sealed, the interior 26 of the pouch 12 can accommodate the pad 14 and cleanser 16. The pad 14 and cleanser 16 are preferably loosely contained in the pouch 12, but can be tightly enclosed, for example by vacuum sealing the pouch 12 about the pad 14 and cleanser 16.

To use the water soluble pouch package, water is poured over the pouch 12. The water dissolves the PVOH film. Once the PVOH dissolves and the water contacts the cleanser 16, the cleanser 16 begins to foam. The chemical reaction between the sodium bicarbonate and citric acid, if used, increases the foam. The cleansing pad absorbs the water and cleansing powder to create a ready-to-use cleansing product. If a cut loofah is used for the pad 14, the loofah expands when placed in contact with the water and absorbs the cleanser 16. The loofah can then be used to exfoliate the skin, with the wetted cleanser 16 providing cleansing foam.

II. Method

Figure 3:
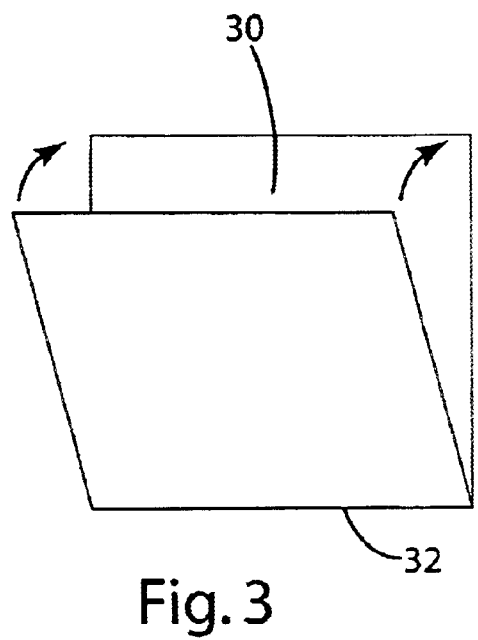
FIG. 3 is a top plan view of the film being folded.
Figure 4:
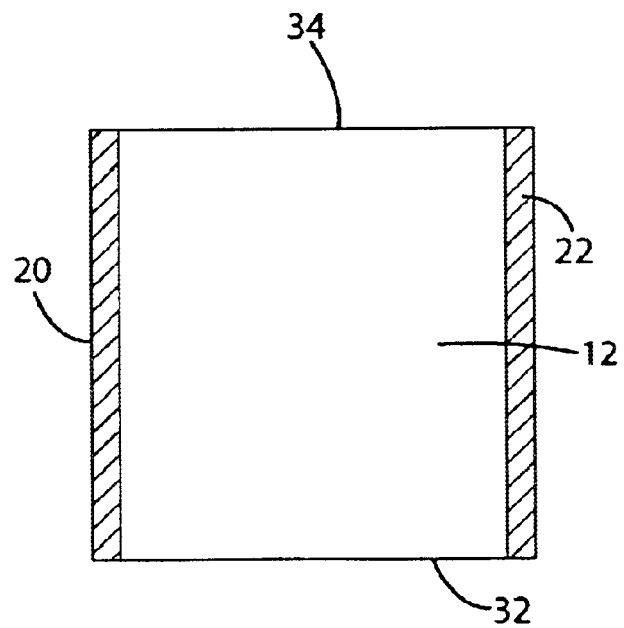
FIG. 4 is a top plan view of the folded film having two sides sealed and including the pad and cleanser.

A method of creating the package 10 of the present invention from a single film 30 will now be more particularly described with reference to FIGS. 2–4. It is to be understood that, though this method is directed to creating the package 10 from a single film, several other methods exist for creating the package 10 of the present invention, such as creating the pouch from two or more films.

Figure 2:
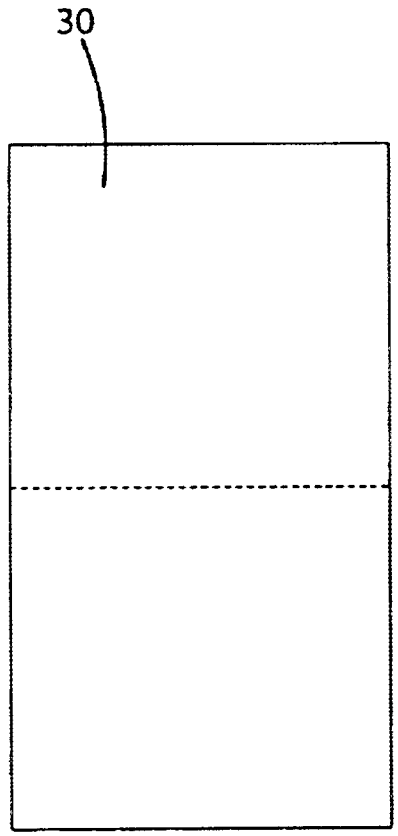
FIG. 2 is a top plan view of a film for forming the pouch in accordance with the present invention.

As can be seen in FIG. 2, the first step in creating the package 10 is to lay a water-soluble film 30 flat. As shown in FIGS. 3 and 4, the film 30 is folded in half, and the left side 20 and right side 22 of the film 30 are sealed. The left side 20 and right side 22 can be sealed by any conventional means, but in a preferred embodiment the sides of the film 30 are heat sealed. The fold 32 creates the bottom of the pouch 12, thus after sealing the left side 20 and right side 22 of the film, only one side, the top 34, remains open.

An opening exists along the top 34 of the pouch 12. The pad 14 and cleanser 16 are inserted through the opening into the pouch 12. The opening must be of sufficient dimensions to allow insertion of both the pad 14 and the cleanser 16. After inserting the pad 14 and cleanser 16, the top 34 of the film 30 is sealed to create a water-soluble package 10. The top 34 of the film 30 can be sealed by a variety of means, but preferably is heat sealed.

The above description is that of a preferred embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The embodiments of the invention in which an exclusive property or privilege is claimed are defined as follows:

1. A unit-dose personal care product comprising:
   a water-soluble pouch loosely containing;
   a cleanser within said pouch; and
   a pad within said pouch, wherein said pad is selected from the group consisting of cloth, loofah and sponge.

2. The product of claim 1, wherein said pouch is formed from a film.

3. The product of claim 2, wherein said film is comprised of a material selected from at least one of the following: polyvinyl alcohol, water-soluble polyurethane, polyvinylpyrrolidone, polyvinylpyrrolidone copolymer, water-soluble acrylic acid copolymer, an ester of a water-soluble acrylic acid copolymer, a salt of a water-soluble acrylic acid copolymer, an organic salt of phenylbenzimidazole sulfonic acid, an inorganic salt of phenylbenzimidazole sulfonic acid, water-soluble cellulosic, water-soluble quaternium, carboxyvinyl polymer, and water-soluble polysaccharide.

4. The product of claim 3, wherein said cleanser is a surfactant powder.

5. The product of claim 4, wherein said cleanser further includes citric acid.

6. The product of claim 5, wherein said cleanser further includes sodium bicarbonate.

7. The product of claim 6, wherein said pad is a non-woven cloth.

8. The product of claim 6, wherein said pad is a cut loofah.

9. A method of manufacturing a personal care product according to claim 1, comprising the steps of:
   a) creating a pouch from a water-soluble material;
   b) inserting a pad into the pouch;
   c) inserting a cleanser into the pouch; and
   d) sealing the pouch.

10. The method of claim 9, wherein step (a) includes the steps of:
    a) laying a water-soluble film flat;
    b) folding the water-soluble film;
    c) sealing the right side of the folded film; and
    d) sealing the left side of the folded film.

11. The method of claim 9, wherein the step of sealing the pouch is performed by heat sealing.

12. The method of claim 10, wherein the step of sealing the right side of the folded film is performed by heat sealing.

13. The method of claim 9 wherein the water soluble material is selected from at least one of the following: polyvinyl alcohol, water-soluble polyurethane, polyvinylpyrrolidone, polyvinylpyrrolidone copolymer, water-soluble acrylic acid copolymer, an ester of a water-soluble acrylic acid copolymer, a salt of a water-soluble acrylic acid copolymer, an organic salt of phenylbenzimidazole sulfonic acid, an inorganic salt of phenylbenzimidazole sulfonic acid, water-soluble cellulosic, water-soluble quaternium, carboxyvinyl polymer, and water-soluble polysaccharide.

* * * * *